(12) United States Patent
Cheong et al.

(10) Patent No.: US 9,499,622 B2
(45) Date of Patent: Nov. 22, 2016

(54) ANTI-EGFR/ANTI-HER2 BISPECIFIC ANTIBODIES WITH ANTI-EGFR DARPINS

(71) Applicant: Samsung Electronics Co., Ltd., Suwon-si, Gyeonggi-do (KR)

(72) Inventors: Kwang Ho Cheong, Seoul (KR); Seung Hyun Lee, Suwon-si (KR); Powei Lin, Hwaseong-si (KR); Saet Byoul Lee, Seoul (KR); Jae Woong Hwang, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/625,296

(22) Filed: Feb. 18, 2015

(65) Prior Publication Data

US 2015/0232573 A1    Aug. 20, 2015

(30) Foreign Application Priority Data

Feb. 18, 2014    (KR) ........................ 10-2014-0018649

(51) Int. Cl.
*C07K 16/30* (2006.01)
*A61K 39/395* (2006.01)
*C07K 16/28* (2006.01)
*C07K 16/32* (2006.01)

(52) U.S. Cl.
CPC ........... *C07K 16/2863* (2013.01); *C07K 16/32* (2013.01); *C07K 2317/31* (2013.01); *C07K 2317/73* (2013.01); *C07K 2317/77* (2013.01); *C07K 2317/92* (2013.01)

(58) Field of Classification Search
CPC ............. C07K 16/00–16/468; C07K 2317/31
See application file for complete search history.

(56) References Cited

U.S. PATENT DOCUMENTS

| 5,677,171 | A | 10/1997 | Hudziak et al. |
| 5,772,997 | A | 6/1998 | Hudziak et al. |
| 5,821,337 | A | 10/1998 | Carter et al. |
| 6,165,464 | A | 12/2000 | Hudziak et al. |
| 7,417,130 | B2 | 8/2008 | Stumpp et al. |
| 8,071,730 | B2 | 12/2011 | Goetsch et al. |
| 8,110,653 | B2 | 2/2012 | Stumpp et al. |
| 8,329,873 | B2 | 12/2012 | Adams et al. |
| 8,524,244 | B2 | 9/2013 | Camphausen et al. |
| 9,234,028 | B2 | 1/2016 | Camphausen et al. |
| 9,359,440 | B2 * | 6/2016 | Cheong ................ C07K 14/705 |
| 2009/0010840 | A1 | 1/2009 | Adams et al. |
| 2010/0178298 | A1 | 7/2010 | Lindhofer |
| 2012/0020966 | A1 * | 1/2012 | Barbas, III ........... C07K 14/515 424/134.1 |
| 2012/0156191 | A1 | 6/2012 | Goetsch et al. |
| 2012/0277143 | A1 | 11/2012 | Jacobs et al. |
| 2013/0017200 | A1 | 1/2013 | Scheer et al. |
| 2015/0030596 | A1 * | 1/2015 | Cheong ................ C07K 14/705 424/134.1 |

FOREIGN PATENT DOCUMENTS

| EP | 1332209 B2 | 11/2009 |
| EP | 2149604 A1 | 2/2010 |
| JP | 2011-517314 A | 6/2011 |
| KR | 2009-0088878 A | 8/2009 |
| KR | 2012-0123299 A | 11/2012 |
| WO | WO 2012/069655 A2 | 5/2012 |

OTHER PUBLICATIONS

HogenEsch et al. J. Controlled Release 2012; 164:183-186.*
Tang et al. Cancer Letters 2016; 370:85-90.*
Kataja et al., Ann Oncol 2009; 20(sup 4): ivl 0-14.*
Nelson et al., Ann. Intern Med. 2009; 151:727-737.*
Balmana et al. Ann Oncol 2009; 20(supp 4):iv19-20.*
Boersma et al., J. Biol. Chem., 2011;286: 41273-85.*
Steiner et al. J. Mol. Biol. 2008; 382:1211-27 and Supplemental Figures.*

* cited by examiner

*Primary Examiner* — Jessica H Roark
(74) *Attorney, Agent, or Firm* — Leydig, Voit & Mayer, Ltd.

(57) ABSTRACT

An anti-EGFR/anti-HER2 bispecific antibody including an anti-EGFR DARPin and an anti-HER2 antibody, a pharmaceutical composition including the bispecific antibody, a method of preparing the bispecific antibody, and a method of reducing a side effect and/or enhancing efficacy of an anti-HER2 antibody using an anti-EGFR DARPin.

19 Claims, 5 Drawing Sheets

ANTI-EGFR/ANTI-HER2 BISPECIFIC ANTIBODIES WITH ANTI-EGFR DARPINS

CROSS-REFERENCE TO RELATED APPLICATIONS

This application claims the benefit of Korean Patent Application No. 10-2014-0018649 filed on Feb. 18, 2014, in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 18,994 bytes ASCII (Text) file named "719349_ST25-revised.TXT," created Feb. 18, 2015 Apr. 29, 2016.

BACKGROUND OF THE INVENTION

1. Field

Provided is an anti-EGFR/anti-HER2 bispecific antibody including an anti-EGFR DARPin and an anti-HER2 antibody, a pharmaceutical composition including the bispecific antibody, a method of preparing the bispecific antibody, and a method of reducing a side effect and/or enhancing an efficacy of an anti-HER2 antibody using an anti-EGFR DARPin.

2. Description of the Related Art

In living cells, various proteins interact with each other and are participants in various disease-causing mechanisms. If at least two of such proteins are simultaneously inhibited, a greater effect of treating a disease and a greater possibility of overcoming a resistance against an inhibitor against each protein can be obtained, compared with the case of inhibiting a single protein. For these reasons, various antibodies capable of inhibiting at least two proteins have been developed.

Although many bispecific antibodies have been developed, most of the bispecific antibodies cannot be commercialized as antibody medicaments, because their therapeutic effects are not clinically verified or various side effects are observed. In addition, the developed bispecific antibodies have defects in stability and large scale production, which is an obstacle in commercialization. The early developed bispecific antibodies having IgG form have difficulties in isolation and purification, since light chains and heavy chains are randomly combined during producing processes, leading to problems in large scale production. In addition, in the case of bispecific antibodies having other form than IgG, the stability as a medicine in respect of protein folding, pharmacokinetics, and the like has not been verified.

Therefore, there is a need for developing a bispecific antibody having increased stability and improved properties as a medicine.

BRIEF SUMMARY OF THE INVENTION

One embodiment provides a bispecific antibody against EGFR and HER2, including an anti-EGFR DARPin and an anti-HER2 antibody.

Another embodiment provides a method of preparing a bispecific antibody against EGFR and HER2, including linking an anti-HER2 antibody and an anti-EGFR DARPin.

Another embodiment provides a pharmaceutical composition including the bispecific antibody.

Another embodiment provides a method of preventing and/or treating a cancer including administering the bispecific antibody to a subject in need of preventing and/or treating the cancer.

Another embodiment provides a method of reducing a side effect (such as agonism) and/or enhancing an efficacy of an anti-HER2 antibody, including binding a DARPin to the antibody.

DETAILED DESCRIPTION OF THE INVENTION

Figure 1:
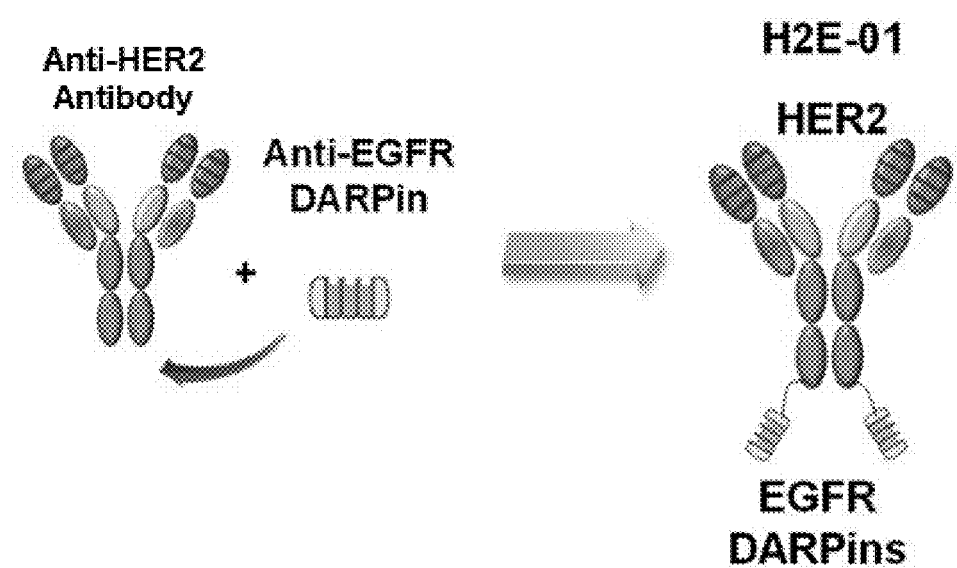
FIG. 1 is a schematic view showing processes of preparing an anti-EGFR/anti-HER2 bispecific antibody.

Bispecific antibodies have been developed in various kinds and forms and are expected as a new drug antibody having excellent therapeutic effects compared to pre-existing monoclonal antibodies, due to its dual (multi-) binding activity to at least two different antigens. Herein, a bispecific antibody obtained by binding a DARPin to an IgG form antibody is disclosed.

DARPin (designed ankyrin repeat protein) refers to an antibody mimetic protein having high specificity and high binding affinity to a target protein, which is prepared via genetic engineering. DARPin is originated from natural ankyrin protein, and has a structure where at least 2 or at least 3 ankyrin repeat motifs, for example, 3, 4, 5, 6, 8 or 10 ankyrin repeat motifs are repeated. For example, the DARPins including 3, 4 or 5 ankyrin repeat motifs may have a molecular weight of about 10 kDa, about 14 kDa, and about 18 kDa, respectively. DARPin includes a core part which acts structural function and a target binding part outside of the core which binds to a target. The core part includes conserved amino acid sequence and the target binding part, which is positioned outside of the core part, includes different amino acid sequence depending on the target.

DARPin has target specificity, which is similar to an antibody, and thus, a new form of a bispecific antibody can be made by attaching at least one DARPin to an antibody having various forms such as an IgG (e.g., IgG1, IgG2, IgG3 or IgG4) form, a scFv-Fc form, and the like.

The "EGFR (epidermal growth factor receptor)" is a member of the receptor tyrosine kinases (RTKs) of HER family. Over-expression, gene amplification, mutation, or rearrangement of EGFR are frequently observed in several human malignant tumors and are related to poor prognosis of cancer treatment and bad clinical outcomes. For such reasons, the EGFR becomes an important target in anticancer therapy.

Therefore, in an embodiment, provided is a fusion protein comprising or consisting essentially of an anti-EGFR DARPin (or an EGFR binding DARPin) which specifically binds to EGFR and an anti-HER2 antibody. The fusion protein may be used as a bispecific antibody specifically recognizing and/or binding to EGFR and HER2. Therefore, another embodiment provides an anti-EGFR/anti-HER2 bispecific antibody comprising or consisting essentially of an anti-EGFR DARPin and an anti-HER2 antibody. The anti-HER2 antibody may be in an IgG form, a scFv-Fc form, or a combination thereof. As used herein, the term "IgG form" may refer to a protein complex composed of four peptide chains, i.e., two identical heavy chains and two identical light chains, arranged in a Y-shape. As used herein, the term "scFv-Fc" may refer to an antibody fragment comprising scFv (single-chain variable fragment; a fusion protein of the variable regions of the heavy (generally at N-terminus) and light chains (generally at C-terminus) of immunoglobulins, connected with each other directly (through a covalent bond such as a peptide bond) or via a peptide linker) and Fc region (fragment crystallizable region) which is linked to the C-terminus of the scFv directly (through a covalent bond such as a peptide bond) or via a peptide linker.

The anti-EGFR DARPin may be any DARPin having DARPin's own unique structure and specifically binding to EGFR. For example, the anti-EGFR DARPin may include at least one selected from the group consisting of the following four anti-EGFR DARPins:

```
anti-EGFR DARPin-01 (SEQ ID NO: 1):
dlgkklleaaragqddevrilmangadvnaddtwgwtplhlaayqghlei vevllkngadvnaydyigwtplhlaadghleivevllkngadvnasdyig dtplhlaahnghleivevllkhgadvnaqdkfgktafdisidngnedlae ilq anti-EGFR DARPin-67 (SEQ ID NO: 2):
dlgkklleaaragqddevrilmangadvnatdndgntplhlsawighlei vevllkhgadvnaddllgmtplhlaadtghleivevllkygadvnardtr gktplhlaardghleivevllkhdadvnaqdkfgktafdisidngnedla eilq anti-EGFR DARPin-68 (SEQ ID NO: 3):
dlgkklleaaragqddevrilmangadvnafdywgmtplhlaadnghlei vevllkhgadvnasdnfgftplhlaafyghleivevllkhgadvnafdmw gntplhlaaqnghleivevllkngadvnaqdkfgktafdisidngnedla eilq anti-EGFR DARPin-69 (SEQ ID NO: 4):
dlgkklleaaragqddevrilmangadvnaddnagrtplhlaanfghlei vevllkngadvnakghhentplhlaawaghleivevllkygadvnaddde gytplhlaadigdleivevllkygadvnawdmygrtplhlaasaghleiv evllkygadvnaqdkfgktafdisidngnedlaeilq
```

HER2 (Human Epidermal growth factor Receptor 2 protein) has been known to play an essential role in controlling proliferation and differentiation of cells. In particular, HER2 strongly tends to assemble with other HER receptors to form a mono-dimer and/or hetero-dimer when extracellular growth factor binds thereto, leading to activation of various signal transduction pathways, thereby inducing apoptosis, survival, or proliferation of cells.

The HER2 protein may be originated from a mammal, for example, HER2 originated from primates, such as human HER2, monkey HER2, and the like, or HER2 originated from rodents, such as mouse HER2, rat HER2, and the like. For example, the HER2 protein may be human HER2 (e.g., encoded by the nucleotide sequence (mRNA) of GenBank Accession Number NM_004448), mouse HER2 (e.g., encoded by the nucleotide sequence (mRNA) of GenBank Accession Number NM_001003817), or rat HER2 (e.g., encoded by the nucleotide sequence (mRNA) of GenBank Accession Number NM_017003).

The antibody having an IgG form may be in a form of IgG1, IgG2, IgG3 or IgG4 subtype of a mammal, for example, IgG1 or IgG2 subtype. The antibody having an IgG form includes two heavy chains and two light chains, and the heavy chain and the light chain are linked to each other via disulfide bond, forming two heavy chain-light chain structures. The formed two heavy chain-light chain structures are linked to each other at Fc region of the heavy chain via disulfide bond.

The antibody having a scFv-Fc form may be in a monomeric form comprising a scFv-Fc fragment comprising an antigen-binding region specifically recognizing and/or binding to HER2 or in a dimeric form comprising two scFv-Fc fragments comprising antigen-binding regions specifically recognizing and/or binding to HER2, where the two scFv-Fc fragments are linked to each other at Fc region. The Fc region may be derived from subtype IgG1, IgG2, IgG3 or IgG4 of a mammal, for example, IgG1 or IgG2.

IgG1, IgG2, IgG3, or IgG4 may originate from a mammal, such as a primate including human, a monkey, and the like, or a rodent including a mouse, a rat, and the like, and for example, may be human IgG1, IgG2, IgG3, or IgG4 subtype.

The anti-HER2 antibody may be (1) an antibody or (2) an IgG type antibody or a scFv-Fc type antibody comprising an antigen-binding region of the antibody (1), wherein the antibody (1) may be selected from the group consisting of:

i) trastuzumab comprising a heavy chain variable region comprising the amino acid sequence of SEQ ID NO: 7 and a light chain variable region comprising the amino acid sequence of SEQ ID NO: 8, ii) pertuzumab comprising a heavy chain comprising the amino acid sequence of SEQ ID NO: 9 and a light chain comprising the amino acid sequence of SEQ ID NO: 10, iii) trastuzumab emtansine (T-DM1), and iv) an anti-HER2 antibody comprising a heavy chain variable region comprising the amino acid sequence of SEQ ID NO: 5 and a light chain variable region comprising the amino acid sequence of SEQ ID NO: 6.

```
<Amino acid sequence of a heavy chain
variable region of an anti-HER2 antibody>
                                    (SEQ ID NO: 5)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS
```

-continued

<Amino acid sequence of a light chain
variable region of an anti-HER2 antibody>
(SEQ ID NO: 6)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKR

The "an antigen-binding region" may refer to a polypeptide comprising a region specifically binding to an antigen (i.e., HER2), and for example, refer to a heavy chain CDR (complementarity determining region), a light chain CDR, a heavy chain variable region, a light chain variable region, or a combination thereof (e.g., scFv, (scFv)2, Fab, Fab', or F(ab')2)) of an anti-HER2 antibody.

The anti-EGFR DARPin may be linked (bound) to C-terminus, N-terminus, or any linkable site of an anti-HER2 antibody having an IgG form or a scFv-Fc form (an IgG type anti-HER2 antibody or a scFv-Fc type anti-HER2 antibody). For example, in order to preserve the antigen-binding ability of the antibody having an IgG form or a scFv-Fc form, the anti-EGFR DARPin may be linked to C-terminus of Fc region of an IgG type anti-HER2 antibody or a scFv-Fc type anti-HER2 antibody, but not be limited thereto. The anti-EGFR DARPin and the anti-HER2 antibody having an IgG form or a scFv-Fc form (an IgG type anti-HER2 antibody or a scFv-Fc type anti-HER2 antibody) may be linked (bound) to each other directly (through a covalent bond such as a peptide bond) or via a proper linker such as a peptide linker.

If the bispecific antibody comprises an anti-EGFR DARPin and a combination of an antibody having an IgG form and an antibody having a scFv-Fc form, the anti-EGFR DARPin, the antibody having an IgG form, and the antibody having a scFv-Fc form may be linked in any order. Although in some cases, the efficacy or expression rate of the bispecific antibody may vary depending on the linking order, in general cases, the linking order has no effect on the desired efficacy of the bispecific antibody. For example, the bispecific antibody may comprise an anti-HER2 antibody having an IgG form, an anti-EGFR DARPin linked to the C-terminus of the anti-HER2 antibody having an IgG form, and an anti-HER2 antibody having a scFv-Fc form linked to C-terminus of the anti-EGFR DARPin, but is not limited thereto.

Another embodiment provides a method of preparing an anti-EGFR/anti-HER2 bispecific antibody, comprising linking an anti-EGFR DARPin and an anti-HER2 antibody. The step of linking an anti-EGFR DARPin and an anti-HER2 antibody may performed by linking the anti-EGFR DARPin, and an anti-HER2 antibody having an IgG form, an anti-HER2 antibody having or a scFv-Fc form, or a combination thereof. When at least two anti-EGFR DARPins are linked, the method may further comprise linking (e.g., linking in series) at least two of anti-EGFR DARPins (for example, 2 to 10, 2 to 5, or 2 to 3 anti-EGFR DARPins, which include the same amino acid sequence, or at least two kinds of DARPins, for example, 2 to 10, 2 to 5, or 2 to 3 kinds of anti-EGFR DARPins, which include different amino acid sequences) to each other, before or after the step of linking the anti-EGFR DARPin, and an anti-HER2 antibody having an IgG form, an anti-HER2 antibody having a scFv-Fc form, or a combination thereof. The anti-HER2 antibody may be an antibody having an IgG form, an antibody having a scFv-Fc form, or a combination thereof.

The bispecific antibody may comprise at least one anti-EGFR DARPin, for example, 1 to 10, 1 to 5, or 1 to 3 anti-EGFR DARPins, which include the same amino acid sequence, or at least two kinds of DARPins, for example, 2 to 10, 2 to 5, or 2 to 3 kinds of anti-EGFR DARPins, which include different amino acid sequences. When the anti-EGFR DARPins include different amino acid sequences, the epitope of EGFR recognized and/or bound by the anti-EGFR DARPins may be the same as or different from each other. In addition to the anti-EGFR DARPin, one or more DARPins, for example, 1 to 10 kinds, 1 to 5 kinds, or 1 to 3 kinds of DARPins, which target other protein than EGFR, may be further included in the bispecific antibody. When at least two DARPins or at least two kinds of DARPins are included, the at least two DARPins or the at least two kinds of DARPins may be linked to each other to form a repeated form and then linked to the antibody (having an IgG form or a scFv-Fc from) in the repeated form, where the DARPins or the repeated form may be linked to at least one of C-terminus, N-terminus, and other linkable site of each chain of the antibody having an IgG form or a scFv-Fc from. For example, the anti-EGFR DARPin may be a repeated form, wherein one or more anti-EGFR DARPins selected from the group consisting of anti-EGFR DARPins comprising the amino acid sequence of SEQ ID NOs: 1, 2, 3, and 4 are repeated 1 to 10 times, 1 to 5 times, or 1 to 3 times, and in this case, the repeated form of anti-EGFR DARPins may be linked to C-terminus, N-terminus, and other linkable site, for example, C-terminus of a heavy chain (e.g., Fc region) or C-terminus of a light chain, of the antibody having an IgG form and/or a scFv-Fc from.

A DARPin and an antibody (e.g., an anti-HER2 antibody) in an IgG form and/or in a scFv-Fc form; a heavy chain variable region and a light chain variable region in the scFv-Fc; and a scFv-Fc and a scFv-Fc (in case of forming a dimer) may be linked to each other with a linker or without a linker (directly, for example, through a peptide bond). The linker may be a peptide linker, and if two or more linkers are used, the linkers may be the same with or different from each other. The peptide linker may comprise 1 to 100 or 2 to 50 of random amino acids, and the kinds of the amino acids comprised in the peptide linker may not have any limitation. For example, the peptide linker may include Gly, Asn and/or Ser residues, or may include neutral amino acids such as Thr and/or Ala. Amino acid sequences suitable for a peptide linker may be well known in the relevant art. The length of the peptide linker may be properly determined so that there is no effect on the function of the bispecific antibody. For example, the peptide linker may include at least one amino acid selected from the group consisting of Gly, Asn, Ser, Thr, and Ala, wherein the total number of the amino acid may be 1 to 100, 2 to 50, or 5 to 25. One embodiment, the peptide linker may be represented as (G4S)n (wherein "n" is repeated number of (G4S), and an integer from 1 to 10, e.g., an integer from 2 to 5).

Since the DARPin has high affinity to an antigen (target), and higher stability and smaller molecular weight than those of general antibody fragment (e.g., scFv, Fab, etc.), the DARPin is advantageous in respect of properties (such as pharmacokinetic (PK) properties in the living body) and stability in the living body. In addition, the DARPin can be readily fused with other protein. Therefore, the DARPin can be useful in preparing a bispecific antibody having excellent properties and stability in the body.

EGFR and HER2, which interact with each other, are representative receptor tyrosine kinase proteins and participate in various tumor-related mechanisms. These proteins can induce proliferation of cancer cells, penetration of cancer cells, angiogenesis, etc. In addition, these proteins interact with each other and participate in each other's signal transduction systems, thereby inducing resistance to treatment of each individually. In addition, the resistance acquired by administration of an EGFR-targeting treatment (Erbitux, Tarceva, Iresa, etc.) is related to over-expression and mutation of HER2. Therefore, simultaneous inhibition of EGFR and HER2 may achieve an increased possibility of overcoming many problems of pre-existing treatments, such as side effects, resistances, and the like, as well as increased therapeutic effect compared to the case of inhibition of a single target. Thus, it is expected that therapeutic effects on cancer, on which pre-existing treatments have no therapeutic effects, can be obtained by simultaneously inhibiting EGFR and HER2.

In addition, the bispecific antibody may make it possible to overcome (acquired) resistance to an anti-HER2 antibody or an EGFR targeting medicament such as an anti-EGFR antibody, thereby being capable of exhibiting the (anticancer) effect even on a cell having the resistance. Therefore, the bispecific antibody comprising an anti-EGFR DARPin and anti-HER2 antibody may have a more increased effect by a degradation mechanism which is distinguished from a pre-existing mechanism.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

An important consideration in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti HER2 antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma ($\gamma$), mu ($\mu$), alpha ($\alpha$), delta ($\delta$), or epsilon ($\epsilon$) type, which may be further categorized as gamma 1 ($\gamma$1), gamma 2 ($\gamma$2), gamma 3 ($\gamma$3), gamma 4 ($\gamma$4), alpha 1 ($\alpha$1), or alpha 2 ($\alpha$2). The light chain constant region is of either a kappa ($\kappa$) or lambda ($\lambda$) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In a particular embodiment, the antigen-binding fragment may be scFv, (scFv)$_2$, scFv-Fc, Fab, Fab', or F(ab')$_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv (scFv) generally includes a heavy chain variable region and a light chain variable region which are linked to each other by a covalent bond via a peptide linker or directly between the C-terminus of the heavy chain variable region and the N-terminus of the light chain variable region or the C-terminus of the light chain variable region and the N-terminus of the heavy chain variable region, to have a dimer structure like the two-chain Fv. The peptide linker may be the same as described herein, for example, those including the amino acid length of 1 to 100, 2 to 50, particularly 5 to 25, and any kinds of amino acids may be included without any restrictions.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-HER2 antibody or an antigen-binding fragment thereof may be modified by the deletion, insertion, addition, or substitution of at least one amino acid residue on the amino acid sequence of the hinge region so that it exhibits enhanced antigen-binding efficiency. For example, the antibody may include a hinge region including the amino acid sequence of SEQ ID NO: 11 (U7-HC6), 12 (U6-HC7), 13 (U3-HC9), 14 (U6-HC8), or 15 (U8-HC5), or a hinge region including the amino acid sequence of SEQ ID NO: 16 (non-modified human hinge). In particular, the hinge region has the amino acid sequence of SEQ ID NO: 11 or 12.

The anti-HER2 antibody having an IgG form may be a monospecific antibody (single targeting antibody) including an antigen-binding region (e.g., a heavy chain CDR, a light chain CDR, a heavy chain variable region, a light chain variable region, or a combination thereof) for HER2 at both of the two heavy chain-light chain structures. Alternatively, the anti-HER2 antibody having an IgG form may be a bispecific antibody targeting two antigens (dual targeting antibody) including an antigen-binding region (e.g., a heavy chain CDR, a light chain CDR, a heavy chain variable region, a light chain variable region, or a combination thereof) for HER2 at one of the two heavy chain-light chain structures, and an antigen-binding region for an antigen other than HER2 at the other heavy chain-light chain structure. In this case, the antigen other than HER2 may be an EGFR.

In another embodiment, the anti-HER2 antibody having an IgG form may be a top and bottom asymmetric bispecific antibody which includes a monospecific antibody in a IgG form including an antigen-binding region for HER2 at both of the two heavy chain-light chain structures and an antigen-binding region (e.g., a heavy chain CDR, a light chain CDR, a heavy chain variable region, a light chain variable region, or a combination thereof (e.g., scFv, (scFv)2, Fab, Fab', or F(ab')2)) for an antigen other than HER2 linked to C-terminus of Fc of the monospecific antibody in a IgG form with or without a linker. In this case, the antigen other than HER2 may be an EGFR. The linker is described as above.

In another embodiment, the anti-HER2 antibody may be an antibody having a scFv-Fc form. The anti-HER2 antibody having a scFv-Fc form may be a monospecific antibody in a monomeric form for targeting HER2, which includes one scFv-Fc fragment including an antigen-binding region (e.g., a heavy chain CDR, a light chain CDR, a heavy chain variable region, a light chain variable region, or a combination thereof) for HER2; a monospecific antibody in a homodimeric form for targeting a single antigen, which includes two scFv-Fc fragments including antigen-binding regions for HER2, where the two scFv-Fc fragments are linked to each other at Fc region; or a bispecific antibody in a heterodimeric form for targeting HER2 and other antigen, which includes a scFv-Fc fragment including an antigen-binding region for HER2 and a scFv-Fc fragment including an antigen-binding region for an antigen other than HER2, where the two scFv-Fc fragments are linked to each other at Fc region. The antigen other than HER2 may be an EGFR.

Another embodiment provides a method of preparing a fusion protein or an anti-EGFR/anti-HER2 bispecific antibody, comprising linking an anti-EGFR DARPin and an anti-HER2 antibody. The step of linking an anti-EGFR DARPin and an anti-HER2 antibody may performed by linking an anti-EGFR DARPin, and an anti-HER2 antibody having an IgG form, an anti-HER2 antibody having or a scFv-Fc form, or a combination thereof. When at least two anti-EGFR DARPins are linked, the method may further comprise linking (e.g., linking in series) at least two of anti-EGFR DARPins (for example, 2 to 10, 2 to 5, or 2 to 3 anti-EGFR DARPins, which include the same amino acid sequence, or at least two kinds of DARPins, for example, 2 to 10, 2 to 5, or 2 to 3 kinds of anti-EGFR DARPins, which include different amino acid sequences) to each other, before or after the step of linking the anti-EGFR DARPin, and an anti-HER2 antibody having an IgG form, an anti-HER2 antibody having a scFv-Fc form, or a combination thereof. The anti-HER2 antibody may be an antibody having an IgG form, an antibody having a scFv-Fc form, or a combination thereof. For example, the step of linking an anti-EGFR DARPin and an anti-HER2 antibody may performed by expressing a recombinant vector in a proper host cell, wherein the recombinant vector comprises a polynucleotide encoding the anti-EGFR DARPin, a polynucleotide encoding the anti-HER2 antibody having an IgG form (i.e., a heavy chain and a light chain of the anti-HER2 antibody) or a scFv-Fc form, or a combination thereof.

Another embodiment provides a pharmaceutical composition comprising the bispecific antibody as an active ingredient. Another embodiment provides a pharmaceutical composition for preventing and/or treating a cancer comprising the bispecific antibody as an active ingredient. Another embodiment provides a method of preventing and/or treating a cancer comprising administering the bispecific antibody to a subject in need of preventing and/or treating a cancer. In the method, the bispecific antibody may be administered in a pharmaceutically effective amount for preventing and/or treating a cancer. The method may further comprise a step of identifying the subject in need of preventing and/or treating a cancer, prior to the step of administering. Another embodiment provides a use of the bispecific antibody for preventing and/or treating a cancer.

The cancer may be a solid cancer or hematological cancer and for instance, may be, but is not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. In particular, the cancer may be cancer having resistance against pre-existing anticancer drugs, for example, antagonists against EGFR. The prevention and/or treatment effects of the cancers may include effects of not only suppressing the growth of the cancer cells but also suppressing progression of cancers due to migration, invasion, and metastasis thereof. Therefore, the curable cancers may include both primary cancers and metastatic cancers.

The bispecific antibody may be administered or formulated along with a pharmaceutically acceptable carrier, diluent, and/or excipient.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition or the bispecific antibody may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage of the pharmaceutical composition or the bispecific antibody may be prescribed in a variety of ways, depending on factors such as formulation methods, administration methods, age of patients, body weight, gender, pathologic conditions, diets, administration time, administration route, excretion speed, and reaction sensitivity. A desirable dosage of the pharmaceutical composition or the bispecific antibody may be in the range of about 0.001 to 100 mg/kg or 0.02 to 10 mg/kg per day for an adult. The term "pharmaceutically effective amount" used herein refers to an amount exhibiting effects in preventing or treating cancer.

The pharmaceutical composition or the bispecific antibody may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition or the bispecific antibody may be administered as an individual drug, or together with other drugs, and may be administered sequentially in any order or simultaneously with pre-existing drugs.

Since the bispecific antibody or the pharmaceutical composition includes an antibody or an antigen binding fragment thereof, it may be formulated as an immunoliposome. The liposome containing an antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction. A chemical drug such as doxorubicin may be additionally included in the liposome.

The subject to which the pharmaceutical composition or the bispecific antibody is administered or the patient to which the prevention and/treatment method is applied may be a mammal, for example, a primate such as human and monkey, or a rodent such as rat and mouse, but are not limited thereto. The subject or the patient may be a cancer patient having resistance against pre-existing anticancer drugs, for example, EGFR antagonists (e.g., an anti-EGFR antibody, etc.) and/or an anti-HER2 antibody.

As described above, DARPin has an excellent properties (e.g., pharmacokinetic (PK) properties) and stability in the body, and thus, when it is fused (linked) with a pre-existing antibody (e.g., an antibody in an IgG form) to prepare a bispecific antibody, it can be achieved not only to simultaneously target at least two antigens including the target of the DARPin but also to enhance the properties and/or stability of the antibody in an IgG form. That is, by fusing a DARPin and a pre-existing antibody in an IgG form, the defect in stability, which is the main problem of the pre-existing bispecific antibody, can be solved, and more increased effect can be achieved.

Accordingly, another embodiment provides a method of enhancement of efficacy or an effect of an anti-HER2 antibody, the method including binding (linking) (a) a DARPin to (b) an anti-HER2 antibody having an IgG form, an anti-HER2 antibody having a scFv-Fc from, or a combination thereof. The DARPin may be at least one anti-EGFR DARPin.

The enhancement of an effect of an antibody (e.g., an anti-HER2 antibody) may include at least one selected from the group consisting of a synergistic effect obtained by targeting at least two antigen, improved properties as a medicament such as pharmacokinetic (PK) properties, increased stability in vivo or ex vivo, overcoming resistance to an anti-HER2 antibody, and decreased side effects of an anti-HER2 antibody.

In the method of enhancement of an effect of an antibody, the DARPin, the anti-EGFR DARPin, the antibody having an IgG form, the antibody having an scFv-Fc form, and their linkage form are described as above.

According to some embodiments, the bispecific antibody comprising an anti-EGFR DARPin and an anti-HER2 antibody may have improved effects compared to pre-existing antibodies, for example, the pre-existing anti-HER2 antibody, as follows:

1. Novel application of EGFR DARPins,
2. Inhibition of EGFR activity by new MOA (mechanism of action)
3. Synergistic anticancer effects compared to pre-existing anti-HER2 antibodies or anti-EGFR antagonists.
4. Anticancer effects on cancer cells having resistance to pre-existing anti-HER2 antibodies or anti-EGFR antagonists.
5. Presentation of a bispecific antibody in an IgG-DARPins form displaying excellent effects compared to combination therapy using an anti-EGFR antibody and an anti-HER2 antibody.

EXAMPLES

Hereafter, the present invention will be described in detail by examples.

The following examples are intended merely to illustrate the invention and are not construed to restrict the invention.

Example 1

Preparation of an Anti-HER2/Anti-EGFR DARPin Bispecific Antibody

The anti-EGFR DARPins was fused to the C-terminus of Herceptin (Roche), to prepare an anti-HER2 antibody/anti-EGFR DARPin fusion complex (i.e., anti-HER2/anti-EGFR bispecific antibody) (FIG. 1). The heavy chain of HERCEPTIN antibody and the anti-EGFR DARPin were linked to each other through a peptide linker having 10 amino acids (GGGGSGGGGS; $(G_4S)_2$ SEQ ID NO: 17), to give "HERCEPTIN heavy chain-$(G_4S)_2$-anti-EGFR DARPins" form.

The prepared anti-HER2/anti-EGFR bispecific antibody was named as "H2E-01".

Example 2

Examination of Properties and EGFR Affinity of the Anti-HER2/Anti-EGFR DARPin Bispecific Antibody To examine properties of the bispecific antibody H2E-01 (anti-HER2/anti-EGFR DARPin bispecific antibody) prepared in Example 1, the bispecific antibody was purified and 20 μg of the bispecific antibody was injected to a HPLC system (WATERS 2695) equipped with TSKG3000SWXL column (Tosho) to the velocity of 0/5 ml/min, to conduct a Size Exclusion Chromatography using HPLC.

Figure 2:
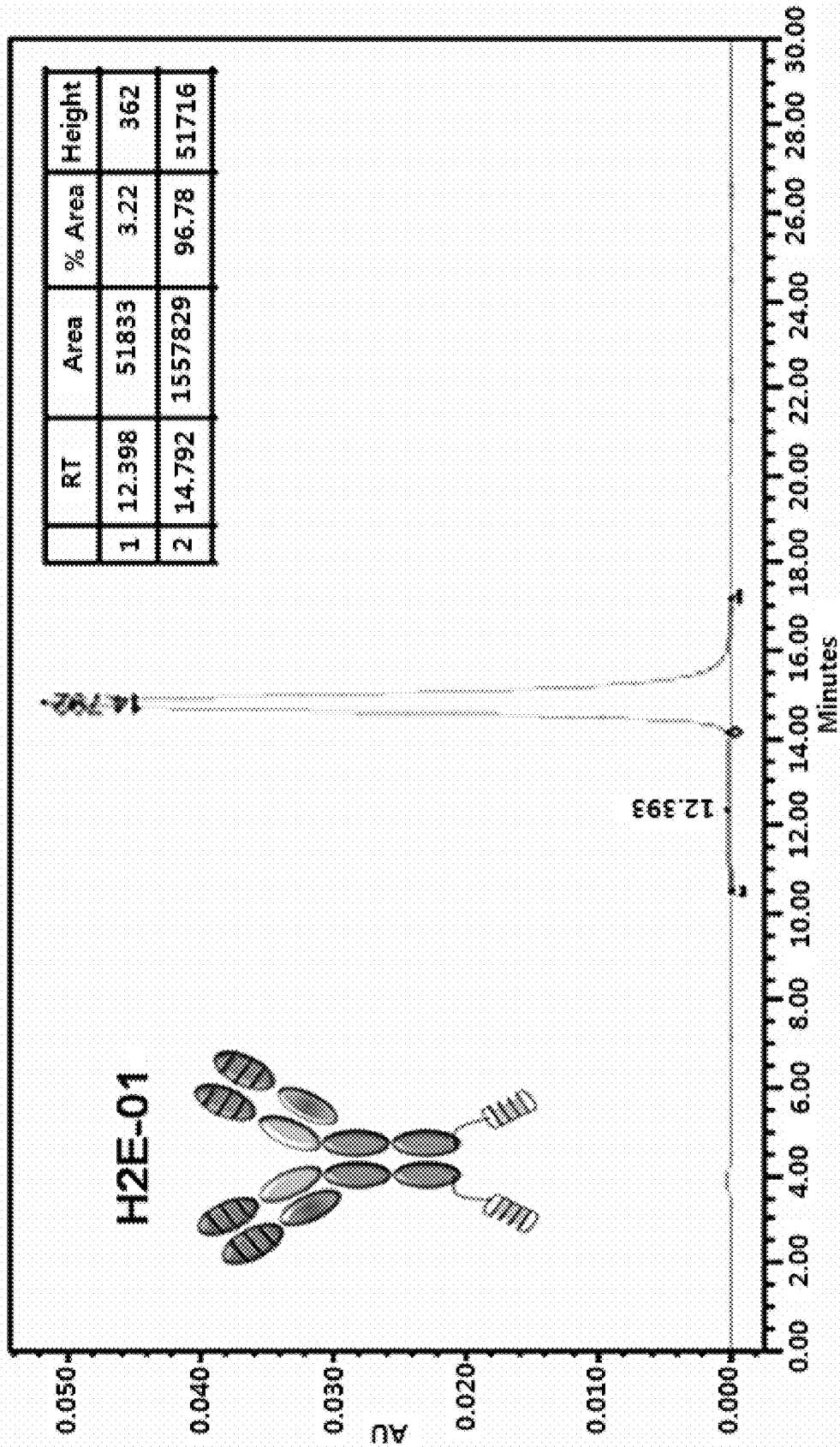
FIG. 2 is a graph showing properties of an anti-EGFR/anti-HER2 bispecific antibody.

The obtained results are shown in FIG. 2. In FIG. 2, "1" refers to a quantitative value of the peak for a soluble dimer, and "2" refers to a quantitative value of the peak for a monomer. As shown in FIG. 2, the anti-HER2/anti-EGFR DARPin bispecific antibody H2E-01 prepared in Example 1 forms very slight amount of soluble dimer (<1), which demonstrates that the bispecific antibody is a very stable molecule.

The binding affinity of bispecific antibody H2E-01 to each of the two antigens HER2 and EGFR was examined using Biacore T100 (GE). Human Fab binder (GE Healthcare) was immobilized on the surface of CM5 chip (#BR-1005-30, GE) according to the manufacturer's manual. About 90~120 RU of the bispecific antibody H2E-01 was captured, and various concentrations of EGFR-Fc (#344-ER, R&D Systems) or HER2-Fc (#1129-ER, R&D Systems) were added to the captured bispecific antibody. 10 mM Glycine-HCl (pH 1.5) solution was added hereto, to regenerate the surface. To determine the affinity, the obtained data were fitted using BIAevaluation software (GE Healthcare, Biacore T100 evaluation software).

The obtained results are shown in Table 1.

Example 3

Examination of Cell Proliferation Inhibition of the Anti-HER2/Anti-EGFR Bispecific Antibody In order to examine the cancer cell proliferation inhibition effect of the bispecific antibody H2E-01 prepared in Example 1, the degree of cell proliferation was tested in MKN45 cell line (KCLB No. 80103), SNU638 cell line (KCLB No. 00683), and N87 cell line (ATCC No. CRL-5822).

Each of the MKN45 cell line, SNU638 cell line, and N87 cell line was cultured in RPMI1640 medium (#11875-093, Gibco) supplemented with 10% (v/v) FBS and 1% (v/v) Penicillin-Streptomycin under the conditions of 5% $CO_2$ and 37° C. To conduct cell proliferation assay, each cell line was sub-cultured in 96-well plate at the concentration of $1 \times 10^4$ cell/well, treated with the anti-HER2/anti-EGFR DARPin bispecific antibody H2E-01 prepared in Example 1 at the amount of 5 μg/ml, and further cultured for 72 hours. A group treated with no antibody was used as a negative control. Groups treated with one of commercially obtained EGFR inhibitor, Erbitux (#ET509081213, Merck; 5 μg/ml), HER2 inhibitor, HERCEPTIN antibody (Trastuzumab, Roche; 5 μg/ml), or a combination thereof were used as positive controls.

After culturing, the cell proliferation was measured by Cell Counting Kit-8 assay (Dojindo Molecular Technologies, Gaithersburg, Md.) according to the manufacturer's manual. In brief, after culturing for 72 hours, 10 μl of CCK8 solution was added to each well, and further cultured 2.5 hours. Then, the absorbance at 450 nm was measured using microplate reader.

Figure 3:
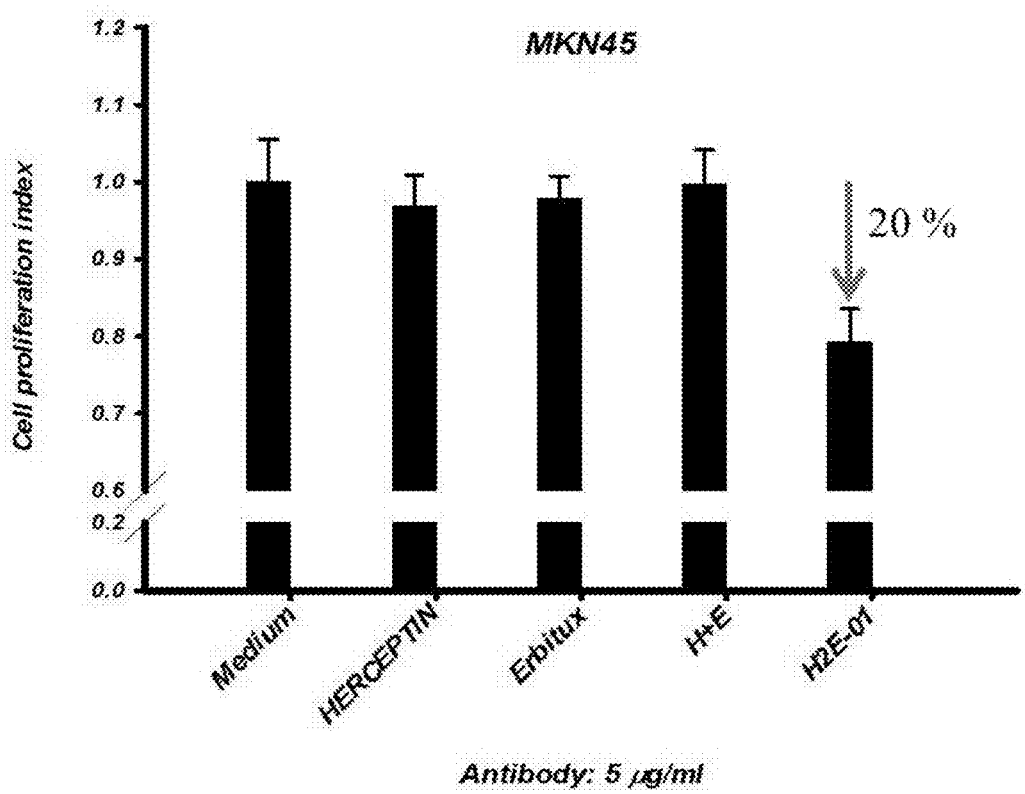
FIG. 3 is a graph showing the degree of proliferation inhibition of MKN45 cells by an anti-EGFR/anti-HER2 bispecific antibody.
Figure 4:
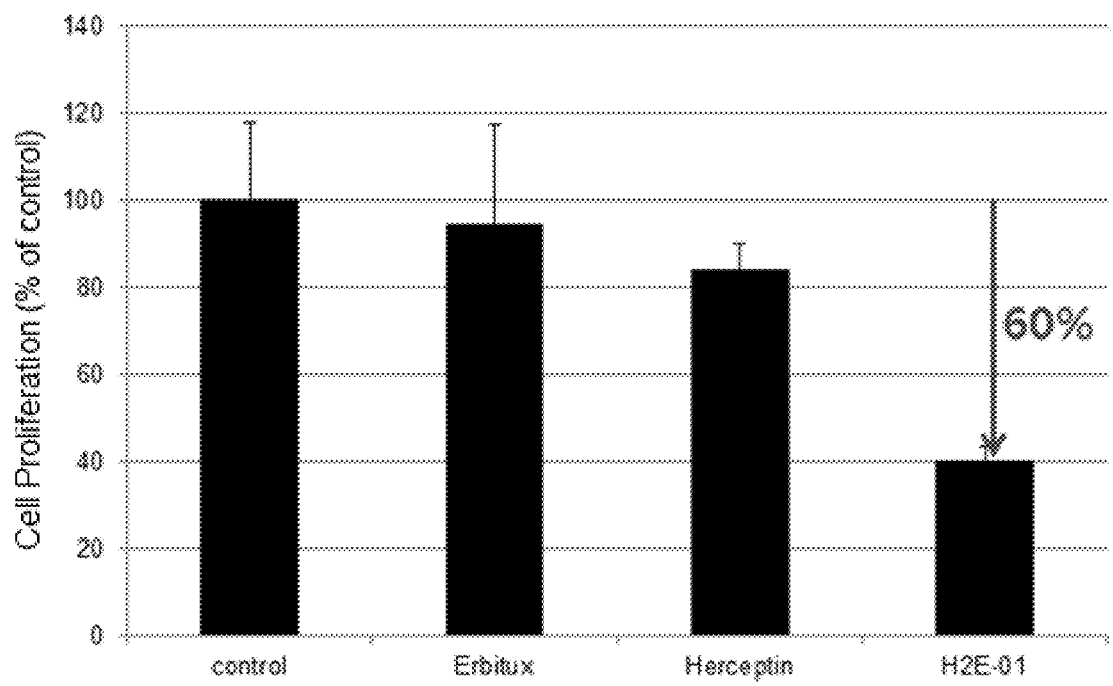
FIG. 4 is a graph showing the degree of proliferation inhibition of SNU638 cells by an anti-EGFR/anti-HER2 bispecific antibody.
Figure 5:
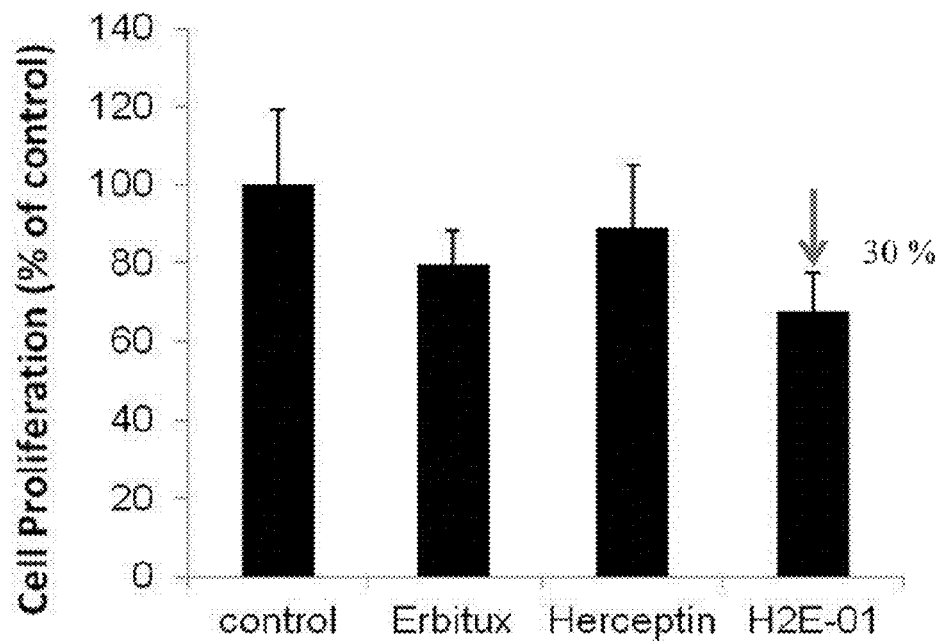
FIG. 5 is a graph showing the degree of proliferation inhibition of N87 cells by an anti-EGFR/anti-HER2 bispecific antibody.

The obtained results are shown in FIG. 3 (MKN45), FIG. 4 (SNU638), and FIG. 5 (N87). As shown in FIGS. 3-5, the anti-HER2/anti-EGFR DARPin bispecific antibody H2E-01 exhibits excellent anticancer effect on gastric cancer cells such as MKN45, SNU638, or N87, compared to Herceptin, Erbitux, and the combination thereof. In addition, Herceptin cannot exhibit a meaningful inhibitory effect on proliferation of gastric cells when administered alone, whereas when Herceptin is fused with an anti-EGFR DARPin, it can exhibit considerable inhibitory effect on proliferation of gastric cells, indicating that anti-EGFR DARPin can enhance the efficacy of Herceptin.

Example 4

Internalization of HER2 and EGFR by the Anti-HER2/Anti-EGFR Bispecific Antibody

Gastric cancer cell line MKN45 (KCLB No. 80103) was provided at the amount of $4 \times 10^4$ cell/well. To the cells,

TABLE 1

| Sample | Antigen | Flow Cell | $R_{max}$ (RU) | $K_D$ (nM) | $k_a$ (1/Ms) | $k_d$ (1/s) | $Chi^2$ | U-Value | $T(K_a)$ | $T(K_d)$ |
|---|---|---|---|---|---|---|---|---|---|---|
| H2E-01 | EGFR-Fc | #4-#1 | 78.89 | 0.03 | $1.0 \times 10^5$ | $<2.8 \times 10^{-5}$ | 1.58 | 95 | $6.2 \times 10^2$ | 1.2 |
| 130522 | Her2-Fc | #2-#1 | 80.45 | <0.01 | $6.9 \times 10^5$ | $<7.5 \times 10^{-5}$ | 1.56 | 95 | $9.8 \times 10^2$ | 1.4 |

As shown in Table 1, the bispecific antibody H2E-01 prepared in Example 1 exhibits very high affinity to EGFR and HER2 as KD=0.03 nM and <0.01 nM, respectively, as measured by Biacore.

Trastuzumab (HERCEPTIN antibody, Roche), CETUXIMAB antibody (Erbitux, #ET509081213, Merck), and anti-HER2/anti-EGFR DARPin bispecific antibody H2E-01 prepared in Example 1 were treated alone or in combination at the amount of 1 μg/ml per each well (when treated in combination, each treated amount is 1 μg/ml), and incubated at 37° C. for 2 hours. The incubated cells were treated with 4% (v/v) formaldehyde for 15 minutes, to be immobilized on plate, and then, washed three times with PBS. Thereafter, the resulted cells were treated with blocking buffer (0.5% (v/v) triton x-100 and 5% (v/v) donkey serum) for 1 hour at room temperature, and then, treated with primary antibodies respectively against HER2 and EGFR (primary antibody for HER2; # 280003Z, Invitrogen, primary antibody for EGFR; #5616, Cell signaling) at the amount of 100 μl (1:100 diluted) at 4° C. for 15 hours. The resultant was washed three times with PBS, treated with a secondary antibody (#A21433, Invitrogen) at the amount of 100 μl (1:2000 diluted) at room temperature for 1 hour, and washed again three times with PBS, to prepare a plate with mounting medium (#H-1200, Vector). The cells in the prepared plate were observed by a confocal microscope (Zeiss, LSM710).

Figure 6:
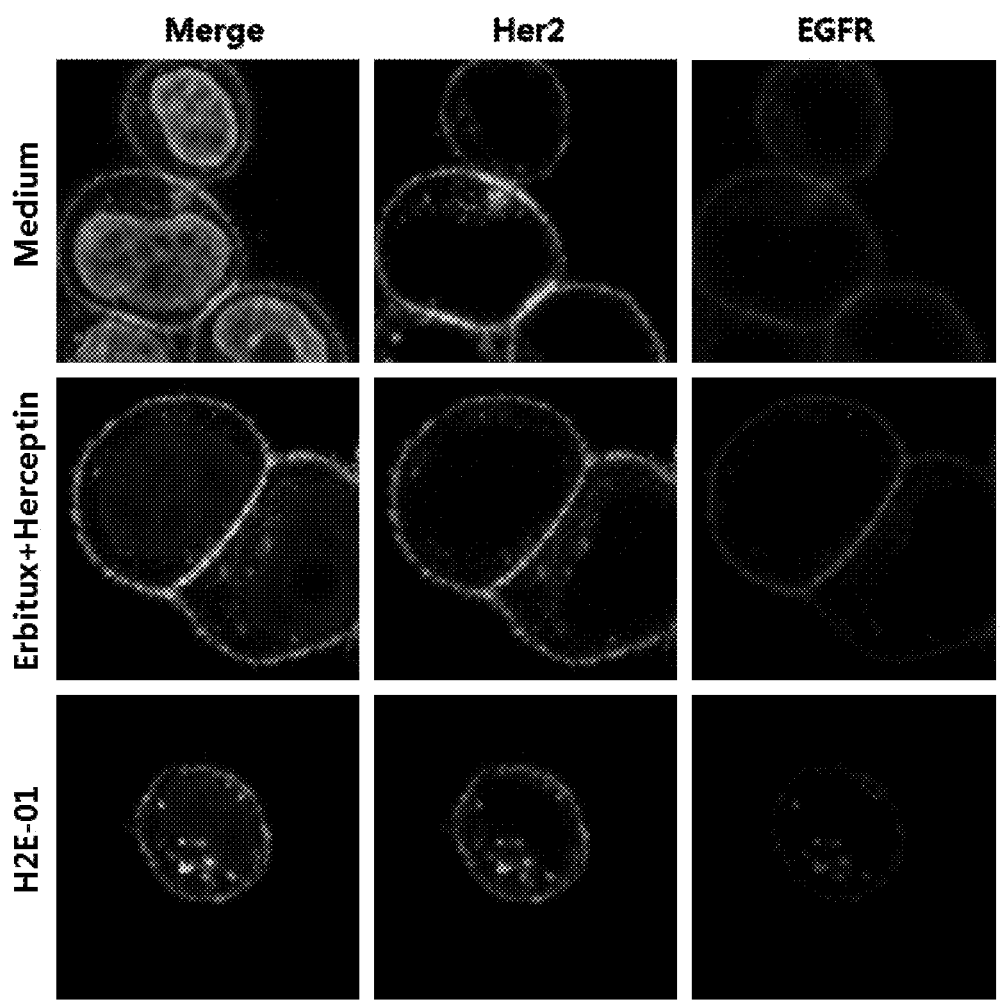
FIG. 6 is a set of fluorescence images showing internalization of EGFR and HER2 by an anti-EGFR/anti-HER2 bispecific antibody.

The obtained results are shown in FIG. 6. As shown in FIG. 6, when Herceptin and Erbitux are treated in combination, EGFR and HER2 still remain on cell membrane, whereas when H2E-01 is treated, both of HER2 and EGFR move into a cell.

In conclusion, the anti-HER2/anti-EGFR DARPin bispecific antibody with an anti-EGFR DARPin inhibits EGFR and HER2 is believed to act by different mechanism from that of pre-existing anti-EGFR or anti-HER2 antibody.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-EGFR/anti-HER2 bispecific antibody comprising:
   an anti-EGFR DARPin, and
   an anti-HER2 antibody, wherein the anti-HER2 antibody is an IgG antibody or an scFv-Fc antibody, or a combination thereof.

2. The bispecific antibody of claim 1, wherein the anti-EGFR DARPin comprises at least one of SEQ ID NO: 1, SEQ ID NO: 2, SEQ ID NO: 3, or SEQ ID NO: 4, and wherein at least one EGFR DARPin is, optionally, repeated 2 to 10 times.

3. The bispecific antibody of claim 1, wherein the anti-HER2 antibody is
   (1) trastuzumab, pertuzumab, trastuzumab emtansine, or an anti-HER2 IgG antibody comprising a heavy chain variable region comprising SEQ ID NO: 5 and a light chain variable region comprising SEQ ID NO: 6; or
   (2) an scFv-Fc antibody comprising an antigen-binding fragment of trastuzumab, pertuzumab, trastuzumab emtansine, or an anti-HER2 IgG antibody comprising a heavy chain variable region comprising SEQ ID NO: 5 and a light chain variable region comprising SEQ ID NO: 6.

4. A pharmaceutical composition comprising the anti-EGFR/anti-HER2 bispecific antibody of claim 1.

5. A method of treating a cancer in a subject, comprising administering the anti-EGFR/anti-HER2 bispecific antibody of claim 1 to the subject, wherein the cancer is characterized by the expression of EGFR and HER2.

6. A method of preparing an anti-EGFR/anti-HER2 bispecific antibody of claim 1, comprising linking
   an anti-EGFR DARPin, and
   an anti-HER2 antibody, wherein the anti-HER2 antibody is an IgG antibody, a scFv-Fc antibody, or a combination thereof.

7. The method of claim 6, wherein the anti-EGFR DARPin comprises at least one of SEQ ID NO: 1, SEQ ID NO: 2, SEQ ID NO: 3, or SEQ ID NO: 4, and wherein at least one EGFR DARPin is, optionally, repeated 2 to 10 times.

8. The method of claim 6, wherein the anti-HER2 antibody is
   (1) trastuzumab, pertuzumab, trastuzumab emtansine, or an anti-HER2 IgG antibody comprising a heavy chain variable region comprising the amino acid sequence of SEQ ID NO: 5 and a light chain variable region comprising the amino acid sequence of SEQ ID NO: 6; or
   (2) a scFv-Fc antibody comprising an antigen-binding fragment of trastuzumab, pertuzumab, trastuzumab emtansine, or an anti-HER2 IgG antibody comprising a heavy chain variable region comprising the amino acid sequence of SEQ ID NO: 5 and a light chain variable region comprising the amino acid sequence of SEQ ID NO: 6.

9. A method of enhancing the efficacy of an anti-HER2 antibody, comprising binding an anti-EGFR DARPin to an anti-HER2 antibody, wherein the anti-HER2 antibody is an IgG antibody, an scFv-Fc antibody, or a combination thereof.

10. The method of claim 9, wherein the anti-EGFR DARPin comprises at least one of SEQ ID NO: 1, SEQ ID NO: 2, SEQ ID NO: 3, and SEQ ID NO: 4, and wherein at least one DARPin is, optionally, repeated 2 to 10 times.

11. The method of claim 9, wherein the anti-HER2 antibody is
    (1) trastuzumab, pertuzumab, trastuzumab emtansine, or an anti-HER2 IgG antibody comprising a heavy chain variable region comprising SEQ ID NO: 5 and a light chain variable region comprising SEQ ID NO: 6; or
    (2) a scFv-Fc antibody comprising an antigen-binding fragment of trastuzumab, pertuzumab, trastuzumab emtansine, or an anti-HER2 IgG antibody comprising a heavy chain variable region comprising SEQ ID NO: 5 and a light chain variable region comprising SEQ ID NO: 6.

12. A nucleic acid encoding the bispecific antibody of claim 1, optionally in a vector.

13. A cell comprising the nucleic acid of claim 12.

14. A method of preparing a bispecific antibody of claim 1 comprising expressing a nucleic acid encoding the bispecific antibody in a cell.

15. The method of claim 5, wherein the subject is a cancer patient having resistance against an EGFR antagonist.

16. The method of claim 5, wherein the subject is a cancer patient having resistance against an anti-HER2 antibody.

17. The method of claim 5, wherein the subject is a cancer patient having resistance against an EGFR antagonist and an anti-HER2 antibody.

18. The antibody of claim 1, wherein treatment of a gastric cancer cell with the antibody causes internalization of HER2 and EGFR.

19. The method of claim 5, wherein the antibody causes internalization of HER2 and EGFR.

* * * * *

SEQUENCE LISTING

```
<160> NUMBER OF SEQ ID NOS: 17

<210> SEQ ID NO 1
<211> LENGTH: 153
<212> TYPE: PRT
<213> ORGANISM: Artificial Sequence
<220> FEATURE:
<223> OTHER INFORMATION: Synthetic anti-EGFR DARPin-01

<400> SEQUENCE: 1

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
             20                  25                  30

Thr Trp Gly Trp Thr Pro Leu His Leu Ala Ala Tyr Gln Gly His Leu
         35                  40                  45

Glu Ile Val Glu Val Leu Leu Lys Asn Gly Ala Asp Val Asn Ala Tyr
     50                  55                  60

Asp Tyr Ile Gly Trp Thr Pro Leu His Leu Ala Ala Asp Gly His Leu
 65                  70                  75                  80

Glu Ile Val Glu Val Leu Leu Lys Asn Gly Ala Asp Val Asn Ala Ser
                 85                  90                  95

Asp Tyr Ile Gly Asp Thr Pro Leu His Leu Ala Ala His Asn Gly His
```

```
                100              105              110
Leu Glu Ile Val Glu Val Leu Lys His Gly Ala Asp Val Asn Ala
            115              120              125

Gln Asp Lys Phe Gly Lys Thr Ala Phe Asp Ile Ser Ile Asp Asn Gly
        130              135              140

Asn Glu Asp Leu Ala Glu Ile Leu Gln
145                 150

<210> SEQ ID NO 2
<211> LENGTH: 154
<212> TYPE: PRT
<213> ORGANISM: Artificial Sequence
<220> FEATURE:
<223> OTHER INFORMATION: Synthetic Anti-EGFR DARPin-67

<400> SEQUENCE: 2

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Thr Asp
                20                  25                  30

Asn Asp Gly Asn Thr Pro Leu His Leu Ser Ala Trp Ile Gly His Leu
            35                  40                  45

Glu Ile Val Glu Val Leu Leu Lys His Gly Ala Asp Val Asn Ala Asp
        50                  55                  60

Asp Leu Leu Gly Met Thr Pro Leu His Leu Ala Ala Asp Thr Gly His
65                  70                  75                  80

Leu Glu Ile Val Glu Val Leu Leu Lys Tyr Gly Ala Asp Val Asn Ala
                85                  90                  95

Arg Asp Thr Arg Gly Lys Thr Pro Leu His Leu Ala Ala Arg Asp Gly
                100                 105                 110

His Leu Glu Ile Val Glu Val Leu Leu Lys His Asp Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 3
<211> LENGTH: 154
<212> TYPE: PRT
<213> ORGANISM: Artificial Sequence
<220> FEATURE:
<223> OTHER INFORMATION: Synthetic Anti-EGFR DARPin-68

<400> SEQUENCE: 3

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Phe Asp
                20                  25                  30

Tyr Trp Gly Met Thr Pro Leu His Leu Ala Ala Asp Asn Gly His Leu
            35                  40                  45

Glu Ile Val Glu Val Leu Leu Lys His Gly Ala Asp Val Asn Ala Ser
        50                  55                  60

Asp Asn Phe Gly Phe Thr Pro Leu His Leu Ala Ala Phe Tyr Gly His
65                  70                  75                  80

Leu Glu Ile Val Glu Val Leu Leu Lys His Gly Ala Asp Val Asn Ala
                85                  90                  95
```

Phe Asp Met Trp Gly Asn Thr Pro Leu His Leu Ala Ala Gln Asn Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 4
<211> LENGTH: 187
<212> TYPE: PRT
<213> ORGANISM: Artificial Sequence
<220> FEATURE:
<223> OTHER INFORMATION: Synthetic Anti-EGFR DARPin-69

<400> SEQUENCE: 4

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
            20                  25                  30

Asn Ala Gly Arg Thr Pro Leu His Leu Ala Ala Asn Phe Gly His Leu
        35                  40                  45

Glu Ile Val Glu Val Leu Leu Lys Asn Gly Ala Asp Val Asn Ala Lys
    50                  55                  60

Gly His His Cys Asn Thr Pro Leu His Leu Ala Ala Trp Ala Gly His
65                  70                  75                  80

Leu Glu Ile Val Glu Val Leu Leu Lys Tyr Gly Ala Asp Val Asn Ala
                85                  90                  95

Asp Asp Asp Glu Gly Tyr Thr Pro Leu His Leu Ala Ala Asp Ile Gly
            100                 105                 110

Asp Leu Glu Ile Val Glu Val Leu Leu Lys Tyr Gly Ala Asp Val Asn
        115                 120                 125

Ala Trp Asp Met Tyr Gly Arg Thr Pro Leu His Leu Ala Ala Ser Ala
    130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 5
<211> LENGTH: 120
<212> TYPE: PRT
<213> ORGANISM: Artificial Sequence
<220> FEATURE:
<223> OTHER INFORMATION: Synthetic heavy chain variable region of
      anti-HER2 antibody

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 6
<211> LENGTH: 108
<212> TYPE: PRT
<213> ORGANISM: Artificial Sequence
<220> FEATURE:
<223> OTHER INFORMATION: Synthetic light chain variable region of
      anti-HER2 antibody

<400> SEQUENCE: 6

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg
            100                 105

<210> SEQ ID NO 7
<211> LENGTH: 220
<212> TYPE: PRT
<213> ORGANISM: Artificial Sequence
<220> FEATURE:
<223> OTHER INFORMATION: Synthetic Heavy chain variable region of
      Trastuzumab

<400> SEQUENCE: 7

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
```

```
                    115                 120                 125
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 8
<211> LENGTH: 214
<212> TYPE: PRT
<213> ORGANISM: Artificial Sequence
<220> FEATURE:
<223> OTHER INFORMATION: Synthetic Light chain variable region of
      Trastuzumab

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 448
<212> TYPE: PRT
<213> ORGANISM: Artificial Sequence
<220> FEATURE:
```

<223> OTHER INFORMATION: Synthetic Heavy chain of Pertuzumab

<400> SEQUENCE: 9

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
     50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 10
<211> LENGTH: 214
<212> TYPE: PRT
<213> ORGANISM: Artificial Sequence
<220> FEATURE:
<223> OTHER INFORMATION: Synthetic Light chain of Pertuzumab

<400> SEQUENCE: 10

Asp Ile Gln Met Thr Gln Ser Pro Ser Ser Leu Ser Ala Ser Val Gly
  1               5                  10                  15
Asp Arg Val Thr Ile Thr Cys Lys Ala Ser Gln Asp Val Ser Ile Gly
             20                  25                  30
Val Ala Trp Tyr Gln Gln Lys Pro Gly Lys Ala Pro Lys Leu Leu Ile
         35                  40                  45
Tyr Ser Ala Ser Tyr Arg Tyr Thr Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Tyr Ile Tyr Pro Tyr
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 11
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 11

Glu Pro Ser Cys Asp Lys His Cys Cys Pro Pro Cys Pro
  1               5                  10

<210> SEQ ID NO 12
<211> LENGTH: 13
```

```
<212> TYPE: PRT
<213> ORGANISM: Artificial Sequence
<220> FEATURE:
<223> OTHER INFORMATION: Synthetic modified hinge region(U6-HC7)

<400> SEQUENCE: 12

Glu Pro Lys Ser Cys Asp Cys His Cys Pro Pro Cys Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 13

Glu Arg Lys Cys Cys Val Glu Cys Pro Pro Cys Pro
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 14

Glu Pro Arg Asp Cys Gly Cys Lys Pro Cys Pro Pro Cys Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 15

Glu Lys Cys Asp Lys Thr His Thr Cys Pro Pro Cys Pro
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 16

Glu Pro Lys Ser Cys Asp Lys Thr His Thr Cys Pro Pro Cys Pro
1               5                   10                  15

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Gly Gly Gly Gly Ser Gly Gly Gly Gly Ser
1               5                   10
```